US010500027B2

(12) United States Patent
Alexander et al.

(10) Patent No.: US 10,500,027 B2
(45) Date of Patent: Dec. 10, 2019

(54) IMPLANTS, TOOLS, AND METHODS FOR TREATMENTS OF PELVIC CONDITIONS

(71) Applicant: Boston Scientific Scimed, Inc., Maple Grove, MN (US)

(72) Inventors: James A. Alexander, Excelsior, MN (US); Justin H. Huelman, Lino Lakes, MN (US); Carrie L. Herman, Mayer, MN (US); Karl A. Jagger, Deephaven, MN (US); Michael A. Knipfer, Maple Grove, MN (US); John R. Frigstad, St. Anthony, MN (US); Robert E. Lund, St. Michael, MN (US); James G. Skakoon, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 234 days.

(21) Appl. No.: 14/795,508

(22) Filed: Jul. 9, 2015

(65) Prior Publication Data

US 2015/0305846 A1 Oct. 29, 2015

Related U.S. Application Data

(62) Division of application No. 13/538,322, filed on Jun. 29, 2012, now abandoned.
(Continued)

(51) Int. Cl.
*A61F 2/00* (2006.01)
*A61B 5/1455* (2006.01)

(52) U.S. Cl.
CPC ........ *A61F 2/0045* (2013.01); *A61B 5/14552* (2013.01); *A61F 2210/0061* (2013.01);
(Continued)

(58) Field of Classification Search
CPC ............ A61F 2/0045; A61F 2210/0061; A61F 2250/0012; A61F 2250/0071;
(Continued)

(56) References Cited

U.S. PATENT DOCUMENTS 3,384,073 A 5/1968 Van Winkle, Jr.
3,789,828 A 2/1974 Schulte
(Continued)

FOREIGN PATENT DOCUMENTS

AU 2002241673 11/2005
CA 2404459 8/2005
(Continued)

OTHER PUBLICATIONS

Herrmann et al. "Nanoparticle films as sensitive strain gauges", Appl. Phys. Lett. 91, 183105 (Year: 2007).*
(Continued)

*Primary Examiner* — Kaylee R Wilson
(74) *Attorney, Agent, or Firm* — Brake Hughes Bellermann LLP

(57) ABSTRACT

Described are various embodiments of surgical procedures, systems, implants, devices, tools, and methods, useful for treating pelvic conditions in a male or female, the pelvic conditions including incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, the devices and tools including devices and tools for anchoring an implant to tissue.

14 Claims, 9 Drawing Sheets

Related U.S. Application Data

(60) Provisional application No. 61/503,137, filed on Jun. 30, 2011.

(52) U.S. Cl.
CPC ............ *A61F 2250/0012* (2013.01); *A61F 2250/0014* (2013.01); *A61F 2250/0071* (2013.01); *A61F 2250/0097* (2013.01)

(58) Field of Classification Search
CPC ...... A61F 2250/0097; A61F 2250/0014; A61F 13/00059; A61F 2013/00123; A61B 5/14552
USPC ...................................... 600/30, 37; 606/151
See application file for complete search history.

(56) References Cited

U.S. PATENT DOCUMENTS

| | | |
|---|---|---|
| 4,548,202 A | 10/1985 | Duncan |
| 4,632,100 A | 12/1986 | Somers et al. |
| 4,873,976 A | 10/1989 | Schreiber |
| 4,938,760 A | 7/1990 | Burton et al. |
| 4,969,892 A | 11/1990 | Burton et al. |
| 4,979,956 A | 12/1990 | Silvestrini |
| 5,013,292 A | 5/1991 | Lemay |
| 5,013,316 A | 5/1991 | Goble et al. |
| 5,019,032 A | 5/1991 | Robertson |
| 5,053,043 A | 10/1991 | Gottesman et al. |
| 5,085,661 A | 2/1992 | Moss |
| 5,112,344 A | 5/1992 | Petros |
| 5,141,520 A | 8/1992 | Goble et al. |
| 5,149,329 A | 9/1992 | Richardson |
| 5,188,636 A | 2/1993 | Fedotov |
| 5,203,864 A | 4/1993 | Phillips |
| 5,209,756 A | 5/1993 | Seedhom et al. |
| 5,256,133 A | 10/1993 | Spitz |
| 5,268,001 A | 12/1993 | Nicholson et al. |
| 5,269,783 A | 12/1993 | Sander |
| 5,328,077 A | 7/1994 | Lou |
| 5,337,736 A | 8/1994 | Reddy |
| 5,354,292 A | 10/1994 | Braeuer et al. |
| 5,362,294 A | 11/1994 | Seitzinger |
| 5,370,662 A | 12/1994 | Stone et al. |
| 5,376,097 A | 12/1994 | Phillips |
| 5,383,904 A | 1/1995 | Totakura et al. |
| 5,520,700 A | 5/1996 | Beyar et al. |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,584,860 A | 12/1996 | Goble et al. |
| 5,591,163 A | 1/1997 | Thompson |
| 5,591,206 A | 1/1997 | Moufarrege |
| 5,628,756 A | 5/1997 | Barker, Jr. et al. |
| 5,643,320 A | 7/1997 | Lower et al. |
| 5,647,836 A | 7/1997 | Blake et al. |
| 5,669,935 A | 9/1997 | Rosenman et al. |
| 5,674,247 A | 10/1997 | Sohn |
| 5,690,655 A | 11/1997 | Hart et al. |
| 5,697,931 A | 12/1997 | Thompson |
| 5,709,708 A | 1/1998 | Thal |
| 5,725,529 A | 3/1998 | Nicholson et al. |
| 5,725,541 A | 3/1998 | Anspach, III et al. |
| 5,741,282 A | 4/1998 | Anspach, III et al. |
| 5,782,862 A | 7/1998 | Bonuttie |
| 5,807,403 A | 9/1998 | Beyar et al. |
| 5,836,314 A | 11/1998 | Benderev et al. |
| 5,842,478 A | 12/1998 | Benderev et al. |
| 5,873,891 A | 2/1999 | Sohn |
| 5,899,909 A | 5/1999 | Claren et al. |
| 5,904,692 A | 5/1999 | Steckel et al. |
| 5,922,026 A | 7/1999 | Chin |
| 5,925,047 A | 7/1999 | Errico et al. |
| 5,934,283 A | 8/1999 | Willem et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,007,539 A | 12/1999 | Kirsch et al. |
| 6,010,447 A | 1/2000 | Kardjian |
| 6,019,768 A | 2/2000 | Wenstrom et al. |
| 6,027,523 A | 2/2000 | Schmieding |
| 6,036,701 A | 3/2000 | Rosenman |
| 6,039,686 A | 3/2000 | Kovac |
| 6,042,534 A | 3/2000 | Gellman et al. |
| 6,042,536 A | 3/2000 | Tihon et al. |
| 6,048,351 A | 4/2000 | Gordon et al. |
| 6,053,935 A | 4/2000 | Brenneman et al. |
| 6,056,688 A | 5/2000 | Benderev et al. |
| 6,068,591 A | 5/2000 | Bruckner et al. |
| 6,077,216 A | 6/2000 | Benderev et al. |
| 6,099,551 A | 8/2000 | Gabby |
| 6,099,552 A | 8/2000 | Adams |
| 6,106,545 A | 8/2000 | Egan |
| 6,110,101 A | 8/2000 | Tihon et al. |
| 6,117,067 A | 9/2000 | Gil-Vernet |
| 6,127,597 A | 10/2000 | Beyar et al. |
| 6,168,611 B1 | 1/2001 | Risvi |
| 6,200,330 B1 | 3/2001 | Benderev et al. |
| 6,221,005 B1 | 4/2001 | Bruckner et al. |
| 6,241,736 B1 | 6/2001 | Sater et al. |
| 6,245,082 B1 | 6/2001 | Gellman et al. |
| 6,264,676 B1 | 7/2001 | Gellman et al. |
| 6,273,852 B1 | 8/2001 | Lehe et al. |
| 6,306,079 B1 | 10/2001 | Trabucco |
| 6,319,272 B1 | 11/2001 | Brenneman |
| 6,322,492 B1 | 11/2001 | Kovac |
| 6,328,686 B1 | 12/2001 | Kovac |
| 6,334,446 B1 | 1/2002 | Beyar |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,423,072 B1 | 7/2002 | Zappala |
| 6,423,080 B1 | 7/2002 | Gellman et al. |
| 6,440,154 B2 | 8/2002 | Gellman et al. |
| 6,451,024 B1 | 9/2002 | Thompson et al. |
| 6,454,778 B2 | 9/2002 | Kortenbach |
| 6,475,139 B1 | 11/2002 | Miller |
| 6,478,727 B2 | 11/2002 | Scetbon |
| 6,491,703 B1 | 12/2002 | Ulmsten |
| 6,506,190 B1 | 1/2003 | Walshe |
| 6,544,273 B1 | 4/2003 | Harari et al. |
| 6,575,897 B1 | 6/2003 | Ory |
| 6,582,443 B2 | 6/2003 | Cabak et al. |
| 6,592,610 B2 | 7/2003 | Beyar |
| 6,599,235 B2 | 7/2003 | Kovac |
| 6,612,977 B2 | 9/2003 | Staskin |
| 6,635,058 B2 | 10/2003 | Beyar et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,685,629 B2 | 2/2004 | Therin |
| 6,702,827 B1 | 3/2004 | Lund |
| 6,730,110 B1 | 5/2004 | Harari et al. |
| 6,746,455 B2 | 6/2004 | Beyar et al. |
| 6,755,781 B2 | 6/2004 | Gellman |
| 6,845,082 B2 | 1/2005 | Bourget et al. |
| 6,881,184 B2 | 4/2005 | Zappala |
| 6,908,425 B2 | 6/2005 | Luscombe |
| 6,908,473 B2 | 6/2005 | Skiba et al. |
| 6,911,002 B2 | 6/2005 | Fierro |
| 6,953,428 B2 | 10/2005 | Gellman et al. |
| 6,960,160 B2 | 11/2005 | Browning |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |

(56) References Cited

U.S. PATENT DOCUMENTS

| | | | |
|---|---|---|---|
| 7,025,063 B2 | 4/2006 | Snitkin | |
| 7,025,772 B2 | 4/2006 | Gellman et al. | |
| 7,048,682 B2 | 5/2006 | Neisz et al. | |
| 7,056,333 B2 | 6/2006 | Walshe | |
| 7,070,558 B2 | 7/2006 | Gellman et al. | |
| 7,083,568 B2 | 8/2006 | Neisz et al. | |
| 7,087,065 B2 | 8/2006 | Ulmsten et al. | |
| 7,112,171 B2 | 9/2006 | Rocheleau et al. | |
| 7,112,210 B2 | 9/2006 | Ulmsten et al. | |
| 7,121,997 B2 | 10/2006 | Kammerer et al. | |
| 7,198,597 B2 | 4/2007 | Siegel et al. | |
| 7,226,408 B2 | 6/2007 | Harari et al. | |
| 7,229,404 B2 | 6/2007 | Bouffier | |
| 7,229,453 B2 | 6/2007 | Anderson | |
| 7,235,043 B2 | 6/2007 | Gellman et al. | |
| 7,261,723 B2 | 8/2007 | Smith et al. | |
| 7,267,645 B2 | 9/2007 | Anderson et al. | |
| 7,291,104 B2 | 11/2007 | Neisz et al. | |
| 7,297,102 B2 | 11/2007 | Smith et al. | |
| 7,303,525 B2 | 12/2007 | Watschke et al. | |
| 7,326,213 B2 | 2/2008 | Benderev et al. | |
| 7,347,812 B2 | 3/2008 | Mellier | |
| 7,351,196 B2 | 4/2008 | Goldmann et al. | |
| 7,351,197 B2 | 4/2008 | Montpetit et al. | |
| 7,364,541 B2 | 4/2008 | Chu et al. | |
| 7,387,634 B2 | 6/2008 | Benderev | |
| 7,402,133 B2 | 7/2008 | Chu et al. | |
| 7,407,480 B2 | 8/2008 | Staskin | |
| 7,410,460 B2 | 8/2008 | Benderev | |
| 7,413,540 B2 | 8/2008 | Gellman et al. | |
| 7,422,557 B2 | 9/2008 | Arnal | |
| 7,431,690 B2 | 10/2008 | Bryon et al. | |
| 7,494,495 B2 | 2/2009 | Delorme et al. | |
| 7,513,865 B2 | 4/2009 | Bourne et al. | |
| 7,527,588 B2 | 5/2009 | Zaddem et al. | |
| 7,547,316 B2 | 6/2009 | Kammerer et al. | |
| 7,588,598 B2 | 9/2009 | Delorme et al. | |
| 7,601,118 B2 | 10/2009 | Smith et al. | |
| 7,621,865 B2 | 11/2009 | Gellman et al. | |
| 7,637,860 B2 | 12/2009 | MacLean | |
| 7,686,759 B2 | 3/2010 | Sater | |
| 7,691,050 B2 | 4/2010 | Gellman et al. | |
| 7,691,052 B2 | 4/2010 | Gellman et al. | |
| 7,722,528 B2 | 5/2010 | Arnal et al. | |
| 7,740,576 B2 | 6/2010 | Hodroff | |
| 7,753,839 B2 | 7/2010 | Siegel et al. | |
| 7,762,942 B2 | 7/2010 | Neisz et al. | |
| 7,762,969 B2 | 7/2010 | Gellman et al. | |
| 7,766,926 B2 | 8/2010 | Bosely et al. | |
| 7,789,821 B2 | 9/2010 | Browning | |
| 7,794,385 B2 | 9/2010 | Rosenblatt | |
| 7,828,715 B2 | 11/2010 | Haverfield | |
| 2001/0000533 A1 | 4/2001 | Kovac | |
| 2001/0023356 A1 | 9/2001 | Raz | |
| 2001/0027321 A1 | 10/2001 | Gellman et al. | |
| 2001/0041895 A1 | 11/2001 | Beyar et al. | |
| 2002/0007222 A1 | 1/2002 | Desai | |
| 2002/0022841 A1 | 2/2002 | Kovac | |
| 2002/0028980 A1 | 3/2002 | Thierfelder et al. | |
| 2002/0035369 A1 | 3/2002 | Beyar et al. | |
| 2002/0050277 A1 | 5/2002 | Beyar | |
| 2002/0055748 A1 | 5/2002 | Gellman et al. | |
| 2002/0058959 A1 | 5/2002 | Gellman et al. | |
| 2002/0072694 A1* | 6/2002 | Snitkin | A61B 17/00234 602/4 |
| 2002/0082619 A1 | 6/2002 | Cabak et al. | |
| 2002/0091373 A1 | 7/2002 | Berger | |
| 2002/0095064 A1 | 7/2002 | Beyar | |
| 2002/0095163 A1 | 7/2002 | Beyar | |
| 2002/0095181 A1 | 7/2002 | Beyar | |
| 2002/0099260 A1 | 7/2002 | Suslian et al. | |
| 2002/0128681 A1 | 9/2002 | Broome et al. | |
| 2002/0138025 A1 | 9/2002 | Gellman et al. | |
| 2002/0147382 A1 | 10/2002 | Neisz et al. | |
| 2002/0151909 A1 | 10/2002 | Gellman et al. | |
| 2002/0156487 A1 | 10/2002 | Gellman et al. | |
| 2002/0156488 A1 | 10/2002 | Gellman et al. | |
| 2002/0161382 A1 | 10/2002 | Neisz | |
| 2002/0188169 A1 | 12/2002 | Kammerer et al. | |
| 2003/0004395 A1 | 1/2003 | Therin | |
| 2003/0009181 A1 | 1/2003 | Gellman et al. | |
| 2003/0023136 A1 | 1/2003 | Raz | |
| 2003/0023137 A1 | 1/2003 | Gellman et al. | |
| 2003/0023138 A1 | 1/2003 | Luscombe | |
| 2003/0036676 A1 | 2/2003 | Scetbon | |
| 2003/0045774 A1 | 3/2003 | Staskin et al. | |
| 2003/0050530 A1 | 3/2003 | Neisz et al. | |
| 2003/0065402 A1 | 4/2003 | Anderson et al. | |
| 2003/0176875 A1 | 9/2003 | Anderson | |
| 2004/0015057 A1 | 1/2004 | Rocheleau et al. | |
| 2004/0039246 A1 | 2/2004 | Gellman et al. | |
| 2004/0039453 A1 | 2/2004 | Anderson et al. | |
| 2004/0073235 A1 | 4/2004 | Lund | |
| 2004/0193215 A1 | 9/2004 | Harari et al. | |
| 2004/0225181 A1 | 11/2004 | Chu et al. | |
| 2004/0267088 A1 | 12/2004 | Krammerer | |
| 2005/0004576 A1 | 1/2005 | Benderev | |
| 2005/0038451 A1 | 2/2005 | Rao et al. | |
| 2005/0131391 A1 | 6/2005 | Chu et al. | |
| 2005/0131393 A1 | 6/2005 | Chu et al. | |
| 2005/0199249 A1 | 9/2005 | Karram | |
| 2005/0245787 A1 | 11/2005 | Cox et al. | |
| 2005/0256530 A1 | 11/2005 | Petros | |
| 2005/0277806 A1 | 12/2005 | Cristalli | |
| 2005/0278037 A1 | 12/2005 | Delorme et al. | |
| 2005/0283189 A1 | 12/2005 | Rosenblatt et al. | |
| 2006/0053903 A1* | 3/2006 | Berenyi | G01L 5/06 73/862.472 |
| 2006/0058578 A1 | 3/2006 | Browning | |
| 2006/0089524 A1 | 4/2006 | Chu | |
| 2006/0089525 A1 | 4/2006 | Mamo et al. | |
| 2006/0122457 A1 | 6/2006 | Kovac | |
| 2006/0173237 A1 | 8/2006 | Jacquetin | |
| 2006/0195007 A1 | 8/2006 | Anderson | |
| 2006/0195011 A1 | 8/2006 | Arnal | |
| 2006/0229493 A1 | 10/2006 | Weiser et al. | |
| 2006/0229596 A1 | 10/2006 | Weiser et al. | |
| 2006/0252980 A1 | 11/2006 | Arnal et al. | |
| 2006/0260618 A1 | 11/2006 | Hodroff et al. | |
| 2006/0287571 A1 | 12/2006 | Gozzi | |
| 2007/0015953 A1 | 1/2007 | MacLean | |
| 2007/0015957 A1* | 1/2007 | Li | A61F 2/0045 600/37 |
| 2007/0078295 A1 | 4/2007 | Iandgrebe | |
| 2007/0088189 A1* | 4/2007 | Levy | A61B 17/42 600/37 |
| 2007/0173864 A1 | 7/2007 | Chu | |
| 2008/0039678 A1 | 2/2008 | Montpetit et al. | |
| 2008/0269548 A1* | 10/2008 | Vecchiotti | A61F 2/0045 600/30 |
| 2009/0005634 A1 | 1/2009 | Rane | |
| 2009/0012353 A1 | 1/2009 | Beyer | |
| 2009/0082617 A1* | 3/2009 | Vecchiotti | A61F 2/0045 600/30 |
| 2009/0221867 A1 | 9/2009 | Ogdahl et al. | |
| 2009/0221868 A1 | 9/2009 | Evans | |
| 2009/0240102 A1 | 9/2009 | Rane et al. | |
| 2009/0259092 A1 | 10/2009 | Ogdahl et al. | |
| 2010/0010631 A1 | 1/2010 | Otte et al. | |
| 2010/0094079 A1 | 4/2010 | Inman | |
| 2010/0152528 A1 | 6/2010 | Chapmenan et al. | |
| 2010/0168595 A1 | 7/2010 | Inman et al. | |
| 2010/0174134 A1 | 7/2010 | Anderson et al. | |
| 2010/0261950 A1* | 10/2010 | Lund | A61F 2/0045 600/30 |
| 2010/0261952 A1 | 10/2010 | Montpetit et al. | |
| 2011/0215601 A1* | 9/2011 | Mueller | B66C 1/12 294/74 |

FOREIGN PATENT DOCUMENTS

| | | |
|---|---|---|
| DE | 20016866 | 3/2007 |
| EP | 0248544 A1 | 12/1987 |

(56) References Cited

FOREIGN PATENT DOCUMENTS

| | | |
|---|---|---|
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 1342450 B1 | 9/2003 |
| FR | 2787990 A1 | 7/2000 |
| FR | 2852817 | 10/2004 |
| IT | 1299162 | 4/1998 |
| WO | WO9310715 A1 | 6/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937216 A1 | 7/1999 |
| WO | WO9937217 A1 | 7/1999 |
| WO | WO9952450 A1 | 10/1999 |
| WO | WO9953844 A1 | 10/1999 |
| WO | WO9958074 A2 | 11/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0030556 A1 | 6/2000 |
| WO | WO0040158 A2 | 7/2000 |
| WO | WO0057796 A1 | 10/2000 |
| WO | WO0057812 A1 | 10/2000 |
| WO | WO0066030 A1 | 11/2000 |
| WO | WO0074594 A1 | 12/2000 |
| WO | WO0074613 A1 | 12/2000 |
| WO | WO0074633 A2 | 12/2000 |
| WO | WO0139670 A1 | 6/2001 |
| WO | WO0145588 A1 | 6/2001 |
| WO | WO0145589 A1 | 6/2001 |
| WO | WO0228312 A1 | 4/2002 |
| WO | WO0228315 A2 | 4/2002 |
| WO | WO0230293 A1 | 4/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02078552 A1 | 10/2002 |
| WO | WO03013392 A2 | 2/2003 |
| WO | WO0303778 A1 | 4/2003 |
| WO | WO03034939 A1 | 5/2003 |
| WO | WO03068107 A1 | 8/2003 |
| WO | WO03073960 A1 | 9/2003 |
| WO | WO03075792 A1 | 9/2003 |
| WO | WO03086205 A2 | 10/2003 |
| WO | WO03092546 A2 | 11/2003 |
| WO | WO03096928 A1 | 11/2003 |
| WO | WO03096929 A1 | 11/2003 |
| WO | WO2004012626 A1 | 2/2004 |
| WO | WO2004016196 A2 | 2/2004 |
| WO | WO2004017862 A2 | 3/2004 |
| WO | WO2004045457 A1 | 6/2004 |
| WO | WO2005004727 A1 | 1/2005 |
| WO | WO2005037132 A2 | 4/2005 |
| WO | WO2005046511 A2 | 5/2005 |
| WO | WO2005048850 A2 | 6/2005 |
| WO | WO2005079702 A1 | 9/2005 |
| WO | WO2005094741 A1 | 10/2005 |
| WO | WO2005112842 A1 | 12/2005 |
| WO | WO2005122954 A1 | 12/2005 |
| WO | WO2006007190 A1 | 1/2006 |
| WO | WO2006015031 A2 | 2/2006 |
| WO | WO2006031879 A1 | 3/2006 |
| WO | WO2006069078 | 6/2006 |
| WO | WO2006108145 A1 | 10/2006 |
| WO | WO2007002012 A1 | 1/2007 |
| WO | WO2007002071 A1 | 1/2007 |
| WO | WO2007011341 A1 | 1/2007 |
| WO | WO2007014241 A1 | 2/2007 |
| WO | WO2007016083 A1 | 2/2007 |
| WO | WO2007016698 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |
| WO | WO-2011082287 A1 * | 7/2011 ........... A61F 2/0045 |

OTHER PUBLICATIONS

Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).

Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).

Benderev, Theodore V., MD, A Modified Percutaneous Outpatient Bladder Neck Suspension System, Journal of Urology, vol. 152, pp. 2316-20 (Dec. 1994).

Benderev, Theodore V., MD, Anchor Fixation and Other Modifications of Endoscopic Bladder Neck Suspension, Urology, vol. 40, No. 5, pp. 409-18 (Nov. 1992).

Blaivas, Jerry et al., Pubovaginal Fascial Sling for the Treatment of Complicated Stress Urinary Incontinence, The Journal of Urology, vol. 145, pp. 1214-1218 (Jun. 1991).

Blaivas, Jerry et al., Type III Stress Urinary Incontinence: Importance of Proper Diagnosis and Treatment, Surgical Forum, pp. 473-475, (1984).

Blavis, Jerry, Commentary: Pubovaginal Sling Procedure, Experience with Pubovaginal Slings, pp. 93-101 (1990).

Bryans, Fred E., Marlex Gauze Hammock Sling Operation with Cooper's Ligament Attachment in the Management of Recurrent Urinary Stress Incontinence, American Journal of Obstetrics and Gynecology, vol. 133, pp. 292-294 (Feb. 1979).

Capio™ CL—Transvaginal Suture Capturing Device—Transvaginal Suture Fixation to Cooper's Ligament for Sling Procedures, Boston Scientific, Microvasive®, 8 pages, (2002).

Choe, Jong M. et al., Gore-Tex Patch Sling: 7 Years Later, Urology, vol. 54, pp. 641-646 (1999).

Dargent, D. et al., Insertion of a Suburethral Sling Through the Obturator Membrane in the Treatment of Female Urinary Incontinence, Gynecol Obstet Fertil, vol. 30, pp. 576-582 (2002).

Decter, Ross M., Use of the Fascial Sling for Neurogenic Incontinence: Lessons Learned, The Journal of Urology, vol. 150, pp. 683-686 (Aug. 1993).

Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.

Falconer, C. et al., Influence of Different Sling Materials of Connective Tissue Metabolism in Stress Urinary Incontinent Women, International Urogynecology Journal, Supp. 2, pp. S19-S23 (2001).

Gynecare TVT Tension-Free Support for Incontinence, The tension-free solution to female Incontinence, Gynecare Worldwide, 6 pages, (2002).

(56) References Cited

OTHER PUBLICATIONS

Handa, Victoria L. et al., Banked Human Fascia Lata for the Suburethral Sling Procedure: A Preliminary Report, Obstetrics & Gynecology, vol. 88 No. 6, 5 pages (Dec. 1996).
Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, p.
Kersey, J., The Gauze Hammock Sling Operation in the Treatment of Stress Incontintence, British Journal of Obstetrics and Gynaecology, vol. 90, pp. 945-949 (Oct. 1983).
Klutke, John M.D. et al., The promise of tension-free vaginal tape for female SUI, Contemporary Urology, 7 pages (Oct. 2000).
Korda, A. et al., Experience with Silastic Slings for Female Urinary Incontience, Aust. NZ J. Obstet Gynaecol, vol. 29, pp. 150-154 (May 1989).
Kovac, S. Robert, et al, Pubic Bone Suburethral Stabilization Sling: A Long Term Cure for SUI?, Contemporary OB/GYN, 10 pages (Feb. 1998).
Morgan, J. E., A Sling Operation, Using Marlex Polypropylene Mesh, For the Treatment of Recurrent Stress Incontinence Am. J. Obst. & Gynecol, pp. 369-377 (Feb. 1970).
Nichols, David H., The Mersilene Mesh Gauze-Hammock for Severe Urinary Stress Incontinence, Obstetrics and Gynecology, vol. 41, pp. 88-93 (Jan. 1973).
Niknejad, Kathleen et al., Autologous and Synthetic Urethral Slings for Female Incontinence, Urol Clin N Am, vol. 29, pp. 597-611 (2002).
Norris, Jeffrey P. et al., Use of Synthetic Material in Sling Surgery: A Minimally Invasive Approach, Journal of Endourology, vol. 10, pp. 227-230 (Jun. 1996).
O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).
Ostergard, Donald R. et al., Urogynecology and Urodynamics Theory and Practice, pp. 569-579 (1996).
Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advanced Surgical Techniques, vol. 9, No. 1 pp. 45-50 (1999).
Ridley, John H., Appraisal of the Goebell-Frangenheim-Stoeckel Sling Procedure, American Journal Obst & Gynec., vol. 95, No. 5, pp. 741-721 (Jul. 1, 1986).
SABRE™ Bioabsorbable Sling, Generation Now, Mentor, 4 pages (May 2002).
SABRE™ Surgical Procedure, Mentor, 6 pages (Aug. 2002).
Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).
Spencer, Julia R. et al., A Comparison of Endoscopic Suspension of the Vesical Neck with Suprapubic Vesicourethropexy for Treatment of Stress Urinary Incontinence, The Journal of Urology, vol. 137, pp. 411-415 (Mar. 1987).
Stamey, Thomas A., M.D., Endoscopic Suspension of the Vesical Neck for Urinary Incontinence in Females, Ann. Surgery, vol. 192 No. 4, pp. 465-471 (Oct. 1980).
Stanton, Stuart L., Suprapubic Approaches for Stress Incontinence in Women, Journal of American Geriatrics Society, vol. 38, No. 3, pp. 348-351 (Mar. 1990).
Stanton, Stuart, Springer-Veglag, Surgery of Female Incontinence, pp. 105-113 (1986).
Studdiford, William E., Transplantation of Abdominal Fascia for the Relief of Urinary Stress Incontinence, American Journal of Obstetrics and Gynecology, pp. 764-775 (1944).
TVT Tension-free Vaginal Tape, Gynecare, Ethicon, Inc., 6 pages (1999).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).
Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).
Vesica® Percutaneous Bladder Neck Stabilization Kit, A New Approach to Bladder Neck Suspension, Microvasive® Boston Scientific Corporation, 4 pages (1995).
Vesica® Sling Kits, Simplifying Sling Procedures, Microvasive® Boston Scientific Corporation, 4 pages (1998).
Walter, Mark D., Percutaneous Suburethral Slings: State of the Art, Presented at the conference of the American Urogynecologic Society, Chicago, 29 pages (Oct. 2001).
Drutz, H.P., et al., Clinical and Urodynamic Re-Evaluation of Combined Abdominovaginal Marlex Sling Operations for Recurrent Stress Urinary Incontinence, International Urogynecology Journal, vol. 1, pp. 70-73 (1990).
Horbach, Nicoliette, Suburethral Sling Procedures, Genuine Stress Incontinence, Chapter 42, pp. 569-579.
Precision Twist, Low Profile design for Precise Anchor Placement, Boston Scientific Microvasive, 2001 2 pp.
Vesica Sling Kit, Microvasive Boston Scientific, 1997, 6pp.
Precision Tack, The Precise Approach to Transvaginal Sling Procedures, Boston Scientific, 1998, 4pp.

\* cited by examiner

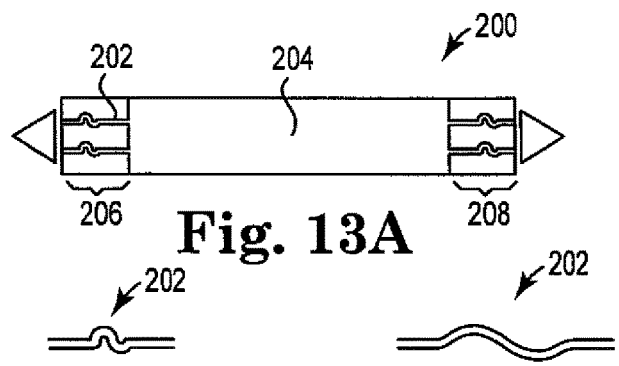
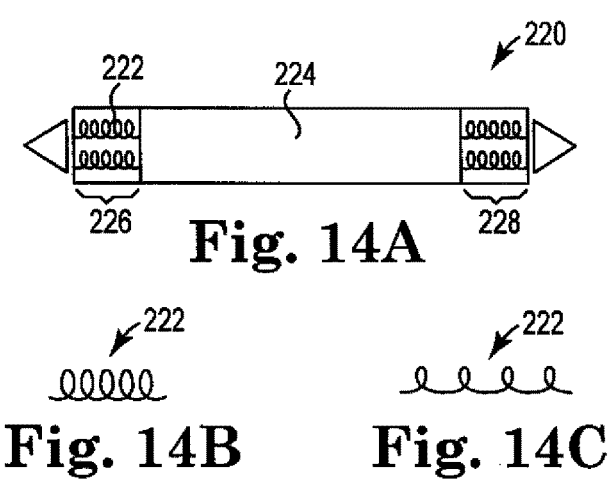
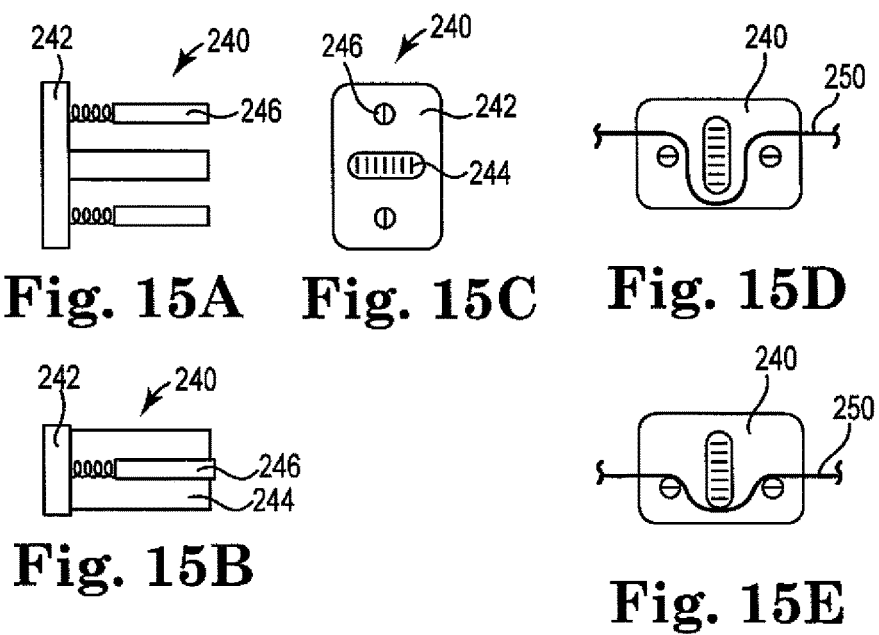

IMPLANTS, TOOLS, AND METHODS FOR TREATMENTS OF PELVIC CONDITIONS

CROSS REFERENCE TO RELATED APPLICATION

This application is a divisional of U.S. application Ser. No. 13/538,322, filed Jun. 29, 2012, which claims the benefit under 35 U.S.C. § 119(e) of U.S. Provisional Patent Application No. 61/503,137, filed Jun. 30, 2011 and titled "Implants, Tools, and Methods for Treatment of Pelvic Conditions", which are incorporated herein by reference in their entireties.

TECHNICAL FIELD

The present invention relates generally to implants, tools, devices, systems, apparatus, and related methods for treating pelvic conditions including but not limited to incontinence and prolapse conditions in men and women.

BACKGROUND

Pelvic health for men and women is a medical area of increasing importance, at least in part due to an aging population. Examples of common pelvic ailments include incontinence (e.g., urinary or fecal), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Urinary incontinence can be characterized by the loss or diminution in the ability to maintain the urethral sphincter closed as the bladder fills with urine. Male or female stress urinary incontinence (SUI) generally occurs when the patient is physically stressed.

Other pelvic floor disorders include cystocele, rectocele, enterocele, and prolapse such as anal, uterine and vaginal vault prolapse. Pelvic disorders such as these can result from weakness or damage to normal pelvic support systems.

In its severest forms, vaginal vault prolapse can result in the distension of the vaginal apex outside of the vagina, and is often associated with a rectocele, cystocele or enterocele. An enterocele is a vaginal hernia in which the peritoneal sac containing a portion of the small bowel extends into the rectovaginal space. Vaginal vault prolapse and enterocele represent challenging forms of pelvic disorders for surgeons. One known method of repairing vaginal vault prolapse is by suturing to the supraspinous ligament or attaching the vaginal vault through mesh or fascia to the sacrum. Many patients suffering from vaginal vault prolapse also require a surgical procedure to correct stress urinary incontinence that is either symptomatic or latent. Many of these procedures often involve lengthy surgical procedure times.

There is therefore a desire to provide a minimally invasive yet highly effective implantable system that can be used to treat incontinence, and/or pelvic organ prolapse and other conditions. Moreover, there is ongoing desire to identify methods and implantable supportive implants that are able to be placed efficiently and effectively within a patient in a manner that provides effective or optimal support, and that can be placed with certain efficacy.

SUMMARY

Devices, systems, and methods as described can be applied to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), levator defects, and other conditions caused by muscle and ligament weakness, hysterectomies and the like.

Various surgical tools, implants, and procedural improvements are disclosed herein. Certain embodiments of methods and implants involve an implant that includes an adjusting mechanism used to adjust a length of the implant (e.g., a length of an extension portion or other portion or piece of an implant) to a desired functional length. Certain embodiments of methods and implants described herein involve an implant adjustment system for use with an implant (e.g., one that includes an elongated mesh) that includes a mesh or other material in which the implantation tension can be measured and/or adjusted (e.g., having one or more dimensions that can be adjusted before, during, or after surgery). Implant and method embodiments can include a tension indicator that is used in cooperation with an implant adjustment system, for example, in order to optimize the effectiveness of the surgical procedure. Embodiments of implants and methods can involve placement of an implant to support pelvic tissue, by way of an incision of minimum size.

BRIEF DESCRIPTION OF THE DRAWINGS

The present invention will be further explained with reference to the appended Figures, wherein like structure is referred to by like numerals throughout the several views, and wherein:

FIGS. 13A-13C are top views of an exemplary embodiment of a tension indicator of the invention positioned relative to an implant;

FIGS. 14A-14C top views of an exemplary embodiment of a tension indicator of the invention positioned relative to an implant;

FIGS. 15A-15C are side, top, and front views, respectively, of a tensioning device of the invention;

FIGS. 15D and 15E are front views of an implant positioned relative to the tensioning device of FIGS. 15A-15C;

DETAILED DESCRIPTION

Figure 1A:
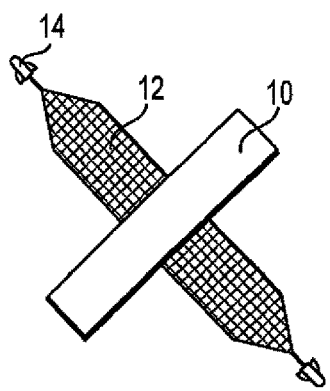
FIG. 1A is a top view of an exemplary embodiment of a tension indicator of the invention positioned relative to an implant.

Pelvic floor disorders include cystocele, rectocele, enterocele, and uterine and vaginal vault prolapse, levator defects, among others, in male and female patients. These disorders typically result from weakness or damage to normal pelvic support systems. The most common etiologies include childbearing, removal of the uterus, connective tissue defects, prolonged heavy physical labor and postmenopausal atrophy.

Vaginal vault prolapse is the distension of the vaginal apex, in some cases to an orientation outside of the vagina. Vaginal vault prolapse is often associated with a rectocele, cystocele or enterocele. It is known to repair vaginal vault prolapse by suturing the vaginal vault (e.g., by stitches) to the supraspinous ligament or by attaching the vaginal vault through mesh or fascia to the sacrum. Many patients suffering from vaginal vault prolapse also require a concurrent or subsequent surgical procedure to correct stress urinary incontinence that is either symptomatic or latent.

In order to place a sling to stabilize or support the bladder neck or urethra, such as for the treatment of incontinence, surgical procedures and devices are often used. There are a variety of different sling procedures, where the slings used for pubovaginal procedures vary widely in the types of material and anchoring methods. In some cases, the sling is placed under the bladder neck and secured via suspension sutures to a point of attachment (e.g., bone) through an abdominal and/or vaginal incision. Examples of sling procedures are disclosed, for example, in U.S. Pat. Nos. 5,112, 344; 5,611,515; 5,842,478; 5,860,425; 5,899,909; 6,039,686; 6,042,534; and 6,110,101.

As used herein, the term "anchor" refers non-specifically to any structure that can connect an implant to tissue of a pelvic region. The tissue may be bone, or a soft tissue such as a muscle, fascia, ligament, tendon, or the like. The anchor may be any known or future-developed structure, or a structure described herein, useful to connect an implant to such tissue, including but not limited to a clamp, a suture, a soft tissue anchor such as a self-fixating tip, a bone anchor, any of the structures described herein to be useful to connect an implant to soft tissue or bone of a pelvic region, or the like.

The systems, devices, tools, implants, etc., described herein are directed to surgical instruments, assemblies, implantable articles, systems and related methods for treating a pelvic condition including prolapse (e.g., any form of vaginal prolapse), urinary and fecal incontinence, levator defects, etc., in a male or female patient. An implant can be implanted in a male or a female to treat a condition such as urge incontinence, mixed incontinence, overflow incontinence, functional incontinence, and the like.

An implant can include a tissue support portion that can be used to support a urethra or other pelvic tissue. Supporting a urethra generally refers to supporting tissue that includes the urethra (which can include the bladder neck) and that can optionally include tissue adjacent to a urethra such as bulbospongiosus muscle, corpus spongiosum, or both. According to specific methods involving treatment of urinary incontinence, a support portion may be placed below bulbospongiosus muscle to support both bulbospongiosus muscle and corpus spongiosum (along with the urethra), or alternately bulbospongiosus muscle may be dissected and a support portion may be placed to contact corpus spongiosum tissue to support the urethra.

An implant can additionally include one or more extension portions (otherwise known as an end portion or arm) attached or attachable to the tissue support portion. Normally, for treating incontinence, an implant can include two opposing extension portions. Extension portions are elongate pieces of material (e.g., mesh, suture, or biologic material) that extend from the tissue support portion and either are or can be connected to the tissue support portion, and are useful to attach to anatomical features or supportive tissue in the pelvic region (e.g., using a self-fixating tip or another form of tissue fastener) to thereby provide support for the tissue support portion and the supported tissue. Generally for treating incontinence, two extension portions can extend from the opposite ends of a tissue support portion as elongate ends, arms, or extensions, and may attach to supportive tissue in the pelvic region by extending through a tissue path to an internal anchoring point (see, e.g., Applicant's copending U.S. Patent Publication No. US 2010/256442, the entirety of which is incorporated herein by reference), or may extend to an external incision, such as through an obturator foramen and through an external incision at a groin or inner thigh (see, e.g., Applicant's copending U.S. Patent Publication Nos. US 2006/0287571 and US 2011/0034759, along with WO 2010/093421, the entireties of which are all incorporated hereby by reference.

In exemplary uses, each extension portion can extend from the location of attachment with the tissue support portion, through pelvic tissue, and optionally be attached to supportive tissue within the pelvic region. For certain procedures, the supportive tissue can be tissue adjacent to the urethra such as pelvic fascia; tissue between the urethra and an obturator foramen such as pelvic fascia; or tissue of an obturator foramen such as obturator fascia, obturator internus muscle, obturator membrane, obturator externus muscle, etc. For alternate procedures an extension portion can be sized to extend from the tissue support portion, through an obturator foramen, around a pubic ramus bone, and threaded (subcutaneously) back to a medial location such as near a medial incision. Other locations for different procedures (e.g., prolapse) include a ligament, tendon, or muscle in the pelvic region such as an arcus tendineus, sacrospinous ligament, or levator muscle.

An implant may include portions, pieces, or sections that are synthetic or of biologic material (e.g., porcine, cadaveric, etc.). Extension portions may be a synthetic mesh, for example, such as a polypropylene mesh, a suture, a biodegradable suture, etc. The tissue support portion may be synthetic (e.g., a polypropylene mesh) or biologic. Examples of implant products that may be similar to those useful according to the present description, include those sold commercially by American Medical Systems, Inc., of Minnetonka Minn., under the trade names "Apogee", "Perigee" and "Elevate" for use in treating pelvic prolapse (including vaginal vault prolapse, cystocele, enterocele, etc.), and under the trade names "Sparc", "Bioarc", "Monarc", "MiniArc", "InVance", and "AdVance" for treating urinary incontinence.

An example of a particular type of pelvic implant is the type that includes supportive portions including or consisting of a tissue support portion and two opposing extension portions extending from the tissue support portion. An implant that has exactly two extension portions can be of the type useful for treating urinary incontinence. The term "supportive portions" refers to portions of an implant that function to support tissue after the implant has been attached within a patient, and specifically includes extension portions and tissue support portions, but does not typically include optional or appurtenant features of an implant such as a sheath, tensioning suture, tissue fastener, or self-fixating tip or other type of connector for attaching the implant to an insertion tool.

An implant (e.g., sling) for placement against a corpus spongiosum for treatment of urinary incontinence in a male patient may optionally and preferably include a widened central support to provide increased contact and frictional engagement with the corpus spongiosum. See, for example, Assignee's copending U.S. Publication No. US 2006/0287571 and U.S. Pat. No. 7,422,557, the entireties of which are both incorporated herein by reference.

Dimensions of a tissue support portion can include any dimensions useful to support urethra tissue for treating incontinence, prolapse, or another pelvic condition. A tissue support portion for use in treating incontinence can be of sufficient length to support and optionally partially surround a urethra or urethra-supporting tissue. A width of a tissue support portion may optionally and preferably be greater than a width of extension portions and can be sufficiently wide to increase contact area and frictional forces between a tissue support portion and a tissue in contact with the tissue support portion. A tissue support portion may be part of a support portion piece that includes the tissue support portion and optionally some amount of opposing extension portions extending from ends of the tissue support portion.

Dimensions of extension portions can allow the extension portion to reach between a tissue support portion placed to support a pelvic tissue, such as tissue of a urethra, vagina, anal sphincter, levator, etc. (at an end of the extension portion connected to the tissue support portion), and a location at which the distal end of the extension portion attaches to supportive tissue at or about the pelvic region. The dimensions in some embodiments can be adjustable, such as the implant length. As described elsewhere herein, a length of an extension portion may be fixed (i.e., the extension portion does not include any form of length-adjustment mechanism) or the implant may include an adjusting engagement that allows a physician to alter the length of an extension portion before, during, and/or after implantation.

Implants as described can include a tissue fastener at a distal end or a distal portion of an extension portion, which is the end or portion not attached to a tissue support portion. As used herein, the term "distal" generally refers to a direction toward a patient and away from a surgeon installing a device. A tissue fastener at a distal end or portion of an extension portion can be any of various types, including: a self-fixating tip that is inserted into soft tissue and frictionally retained; soft tissue anchors; biologic adhesive; a soft tissue clamp that can generally include opposing, optionally biased, jaws that close to grab tissue; and opposing male and female connector elements that engage to secure an end of an extension portion to tissue. (See International Patent Application No. PCT/US2007/014120; U.S. patent application Ser. Nos. 12/223,846 and 12/669,099; and WO 2009/075800, the entireties of which are all incorporated herein by reference). An implant may also have one or more extension portions that do not include a tissue fastener, such as may be used if the distal end is designed to be secured to tissue by other methods (e.g., suturing), or is intended to pass through an obturator foramen and a tissue path around a pubic ramus bone, in which case the extension portion may optionally include a connector, dilator, or dilating connector, which connects to an elongate tool that can be used to either push or pull the connector, dilator, or dilating connector through a tissue path (e.g., to a medial incision).

One embodiment of a tissue fastener is a self-fixating tip. In general, a self-fixating tip can be a structure (sometimes referred to as a soft tissue anchor) connected at a distal end of an extension portion (or extension portion piece) that can be implanted into soft tissue (e.g., muscle, fascia, ligament, etc.) in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through and into tissue for implantation, preferably also through a medial incision to reach the interior of the pelvic region, e.g., at a location of an obturator foramen. The insertion tool may engage the self-fixating tip at an internal channel of the self-fixating tip, at an external location such as at an external surface of the base, at a lateral extension, or otherwise as desired, optionally in a manner to allow the insertion tool to push the self-fixating tip through an incision in a patient and through and into supportive tissue.

Exemplary self-fixating tips can include one or more lateral extensions that allow the self-fixating tip to be inserted into soft tissue and to become effectively anchored in the tissue. A lateral extension may be moveable or fixed. The size of the self-fixating tip and optional lateral extensions can be useful to penetrate and become anchored into the tissue. Exemplary self-fixating tips are described in Assignee's copending international patent application PCT US2007/004015, the entirety of which is incorporated herein by reference. Other structures may also be useful.

According to exemplary embodiments, a self-fixating tip can have structure that includes a base having a proximal base end and a distal base end. The proximal base end can be connected (directly or indirectly, such as by a connective suture) to a distal end of an extension portion. The base extends from the proximal base end to the distal base end and can optionally include an internal channel extending from the proximal base end at least partially along a length of the base toward the distal base end. The optional internal channel can be designed to interact with (i.e., engage, optionally by means of a release mechanism that can be selectively engaged and released) a distal end of an insertion tool to allow the insertion tool to be used to place the self-fixating tip at a location within pelvic tissue of the patient. A self-fixating tip can be made out of any useful material, generally including materials that can be molded or formed to a desired structure and connected to or attached to a distal end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

According to various systems as described, one or more instruments, insertion tools, adjusting tools, or the like, may be incorporated or used with an implant or method as described. Examples of useful tools include those that generally include one or more (stationary or moveable) thin elongate, relatively rigid shafts or needles that extend from a handle. The shaft can be a single elongate shaft or multiple separate elongate shafts extending from the handle, or one or more primary shafts that extend from the handle and that contain multiple branch or "tine" shafts that separate at the end of the primary shaft. The handle is located at a proximal end of the device and attaches to one end (a proximal end) of a shaft. According to some embodiments, a distal end of one or more shafts can be adapted to engage a portion of an implant, such as a tissue fastener (e.g., a self-fixating tip), in a manner that allows the insertion tool to engage and push the tissue fastener through a tissue passage and connect the tissue fastener to supportive tissue of the pelvic region. Examples of this type of tool can be used with a self-fixating tip that includes an internal channel designed to be engaged by a distal end of an insertion tool to allow the self-fixating tip to be pushed into tissue. Other general types of insertion tools will also be useful, but may engage a self-fixating tip or other tissue fastener in an alternate manner, e.g., that does not involve an internal channel.

Exemplary insertion tools for treatment of incontinence and vaginal prolapse are described, e.g., in U.S. patent application Ser. Nos. 10/834,943; 10/306,179; 11/347,553; 11/398,368; and 10/840,646; PCT Application Nos. 2006/028828 and 2006/0260618; WO 2010/093421; and U.S. Patent Publication No. US 2010/0256442, wherein the entirety of these documents are incorporated herein by reference.

A tool that can be used for embodiments of the invention can optionally include a mechanism by which a tissue fastener (e.g., a self-fixating tip) can be securely and releasable engaged with a distal end of an insertion tool such that the tissue fastener can be selectively secured to the distal end mechanically, then selectively released. With a releasable engagement, a tissue fastener (e.g., self-fixating tip) can be released from the distal end by releasing the engagement (e.g., mechanical engagement) by movement of an actuator at the proximal end of the insertion tool, such as at the handle. Optionally, an implant can include a tissue fastener at a location of a tissue support portion, or at a location along a length of an extension portion. This form of tissue fastener can be in the form of reinforced (e.g., by coating, heat treating, or a reinforcing weave or strip) edge extensions, multiple layers of mesh and edge extensions in an extension portion, etc., as described, for example, at Applicant's copending U.S. Pat. No. 7,422,557, and Applicant's copending United States Patent Publication Nos. US 2006/0195011, US 2006/0195007, and US 2006/0195010, all of which are incorporated herein by reference.

Other examples include relatively rigid structures such as metal, plastic, or other polymeric or non-polymeric structure that may be shaped to frictionally engage soft tissue, for example to include a tine, hook, chevron, barb, arrow, etc., combinations thereof, or any structure added to an edge or surface of an extension portion to improve fixation within tissue. The structure can have any shape or form that will increase frictional force between the implant and adjacent tissue, such as one or multiple pointed surface directed along a length of an extension portion, toward the tissue support portion, and extending away from a surface or edge of the implant (e.g., extension portion). The tissue fastener can be located at a position of an implant that will result in the tissue fastener being located at supportive tissue such as muscle or fascia when the implant is placed with a midline of the tissue support portion being located below a urethra. For example, a tissue fastener may be located on a tissue support portion or an extension portion of an implant, e.g., as close as 2 or 3 centimeters from a midline of a tissue support portion, and up to a distance that reaches tissue of an obturator foramen when the midline is located below a urethra, e.g., up to 7 centimeter from the midline.

According to embodiments of implants described herein, an implant can include multiple pieces that are adjustably connected together by an adjusting engagement. A multi-piece implant refers to an implant that includes a support portion piece and one or multiple extension portion pieces. as separate pieces of the implant. An extension portion piece can be separate from a support portion piece, and the two pieces can be connected through an adjustable engagement. The support portion piece includes a tissue support portion.

An adjusting engagement may be, for example, a one-way adjusting engagement, a two-way adjusting engagement, or a locking two-way engagement, that allows a portion, piece, or a segment of an implant to be moved relative to another portion, piece, or segment if the implant and adjusted as to length, tension, or positioning. Examples of adjusting engagements are described, for example, in Applicant's copending U.S. patent application Ser. Nos. 12/308,436 and 12/669,099, the entireties of which are incorporated herein by reference.

Some adjusting engagements can allow two-way movement of one piece relative to another piece (e.g., a "two-way" adjusting engagement). This type of adjusting engagement allows movement of a segment of implant (e.g., of a segment or portion of an extension portion piece) in two directions through an adjusting engagement. Other adjusting engagements may allow for one-way adjustment such as shortening of a length of an extension portion. These adjusting engagements can be referred to as "one-way" adjusting engagements, and allow adjustment of a length of an implant portion (e.g., extension portion) in one direction and not (or not easily) in an opposite direction.

One form of implant useful for treatment of urinary incontinence is a "mini-sling," or "single incision sling" (e.g., as marketed by American Medical Systems under the trade designation "MINIARC"), which has entered the market as a faster more minimally invasive procedure for treating female stress urinary incontinence. The adjustability on currently released traditional slings (such as retropubic and transobturator) in minimal. Adjustability of a sling allows for a broader use among physicians for a more diverse patient population. Designs described herein are also useful for female pelvic floor repair products, male incontinence, for treating prolapse (e.g., vaginal prolapse), levator defects, anal incontinence, and other pelvic conditions. In particular, methods and devices useful for a transvaginal approach of placing an implant for a treatment of a pelvic condition in a male or female anatomy, e.g., a sacrocolpopexy in a female anatomy, are shown and described.

As is illustrated and described herein, a tension indicator, which also may be referred to an a tension feedback indicator or indicator, generally includes a device associated with an implant that allows for a user (e.g., surgeon or doctor) to identify a level of tension applied to an implant or portion of an implant such as an extension portion or a tissue support portion, during a surgical procedure for implanting the implant in a patient. Certain tension feedback indicators as described herein can allow for simple visual indication of tension applied to an implant segment (e.g., a mesh segment) during a surgical procedure of placement of a surgical implant into the patient. Any of the tension feedback indicators can be used with an implant of the type that, during installation, includes a tension or length that is desirably measured or understood. These may include any of the implants generically or specifically described herein that either include or do not include an adjustment mechanism (e.g., an adjusting engagement or other form of adjustment mechanism), and/or any implant previously or presently known to be useful for treating a pelvic condition, and implants developed in the future for treating a pelvic condition.

A tension indicator can allow for simple and easy measurement and indication of an amount of tension placed on a length of implant or a piece or portion of an implant (e.g., an extension portion or a tissue support portion) during placement of the implant in a patient. This may eliminate the need for additional tools or measurement devices, as the sling itself provides feedback. The feedback is provided as the implant is being placed, so there is no need to pause during placement to check tension then re-engage and finish placement. This allows a surgeon to apply consistent tension during placement of an implant.

A tension feedback indicator can be a device placed onto a portion of an implant, such as a length of an elongate portion of an implant that will be affected based on the degree of tensioning of a length of the portion of implant. Generally a length of implant will stretch or lengthen when tension is placed on the length of implant. A tension feedback indicator that is attached to that length of implant can change form based on the changing or changed length of the implant. As an example, a tension feedback indicator may change shape, such as a length, upon tensioning of an implant portion to which the tension feedback indicator is attached. The degree or extent of the change in shape (e.g., length) can indicate the amount of tension that is being placed along the length of implant.

These and other types of tension feedback indicators can include an overall structure that includes a central, deformable or flexible segment located between two fixed or non-flexible segments that attach to an implant. When the end segments are attached to an implant and the implant is lengthened, the deformable segment is deformed in a manner that allows the central portion to become lengthened, and the attached end segments are not substantially deformed but remain attached to the lengthening implant. The flexible segment allows the indicator to lengthen upon lengthening of the implant to which the tension feedback indicator is attached, and can preferably return to a non-lengthened form when tension in the implant is released.

Figure 1B:
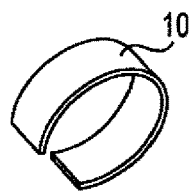
FIG. 1B is a perspective view of the tension indicator of FIG. 1A.
Figure 1C:
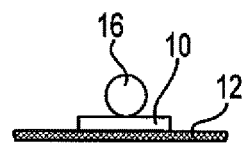
FIG. 1C is a side view of the tension indicator and implant of FIG. 1A.

Referring now to the Figures, and initially to FIGS. 1A-1C, an exemplary embodiment is illustrated of a tension indicator that can be used with implants of the type described herein. In particular, a shape-changing tension indicator 10 is illustrated, which is a device/tool that changes shape when a particular force is applied to it and/or a particular force is removed. The tension indicator 10 is shown in one exemplary location relative to an exemplary mesh implant 12 that includes anchors 14 at its distal ends. As illustrated in FIG. 1A, the shape-changing tension indicator 10 is initially configured to be a rectangular and flat piece of material, although it can instead have a different shape. The tension indicator 10 is designed to have a structure that keeps it relatively rigid when it is in this flat or planar condition, such as can be accomplished with a thin metal frame covered by a flexible covering material, for example. The tension indicator 10 can be positioned for functional communication with the mesh implant 12, for example, and in the exemplary application illustrated in FIG. 1C, the tension indicator 10 is shown as being positioned between a mesh implant 12 and the urethra 16 of a patient. When a particular tension is reached in the tension indicator 10 during the process of implanting the mesh implant, it can collapse or curl from its relatively flat configuration to a curved configuration, such as is illustrated in FIG. 1B. The curling or other deformation of the tension indicator will indicate to the surgeon that a certain tension level has been reached.

Tension indicator 10 may have a wide variety of shapes and sizes for functional communication with various mesh implants 12 and for use in various applications. It is contemplated that more than one of such tension indicators 10 can be used with a single implant, wherein each of the implants will be "activated" (i.e., changed from one configuration to another) at the same or different tension as the other tension indicators that are in communication with that implant. It is further understood that a reconfiguration of this type of tension indicator from one state to another may include rolling or curling in the opposite direction from shown, or that the reconfiguration may include folding, bending, and/or other deformation in more than one direction.

Figure 2:
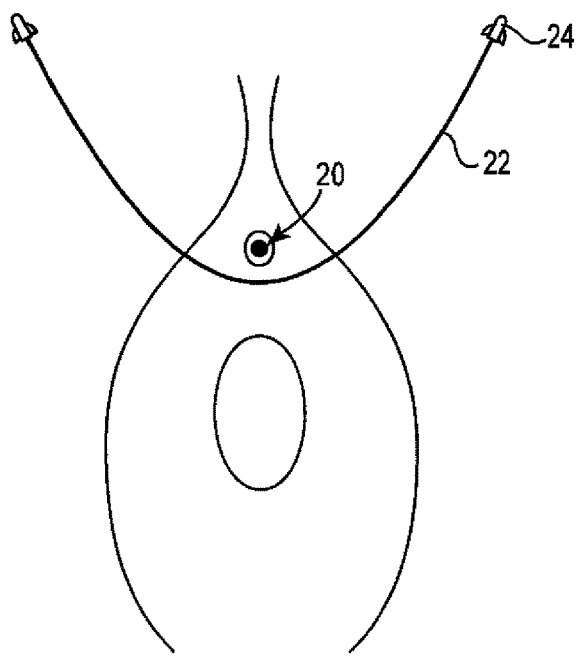
FIG. 2 is a front schematic view of a tension indicator of the invention located relative to an anatomical location of a patient.

FIG. 2 illustrates another embodiment of a manner and device for measuring tension of an implant, such as a sling 22 having anchor members 24 at its distal ends, during a sling implantation procedure. In this embodiment, a measurement of tissue surrounding or adjacent to the implant area can be used as an indirect measurement of sling tension. The desired measurement may be taken by a probe 20 or other device that is placed in the tissue adjacent to the area where the sling is being implanted. In one example, the pH of the tissue surrounding the urethra can be measured and monitored, wherein the sling 22 is being implanted to support the urethra. In another example, a pulse oximeter is used to indirectly monitor the oxygen saturation of a patient's blood during the process of achieving the correct tension in the sling.

Figure 3:
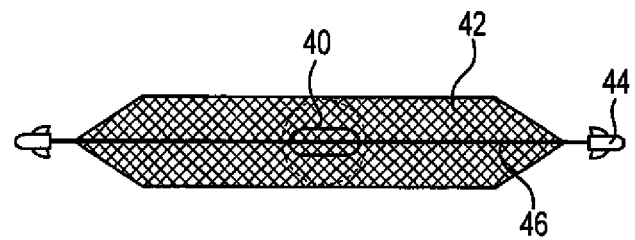
FIG. 3 is a top view of an exemplary embodiment of a tension indicator of the invention positioned relative to an implant.
Figure 4:
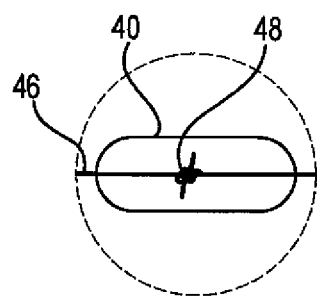
FIG. 4 is an enlarged view of the tension indicator of FIG. 3.

Another embodiment of a tension indicator is illustrated in FIGS. 3 and 4, which includes a capsule 40 that is at least partially filled with liquid and which is functionally associated with an implant 42 and a suture 46. Suture 46 extends beyond the ends of the implant 42, which may be made of a mesh material, for example, and may include anchors 44 at both of its ends. In one example, the suture 46 is attached to the capsule 40 by wrapping or tying it around the capsule 40 at a knot 48, as is illustrated in FIG. 4, although the suture 46 may be otherwise associated with or attached to the capsule 40, such as with an adhesive or other attachment means. The suture 46 and capsule 40 are positioned to be in functional engagement with the implant 42 (e.g., a urethral sling or other form of implant) having two ends and an anchor 44 at each end, such that increasing the tension on the implant 42 will cause a corresponding increase in the tension in the suture 46. During the process of securing the implant 42 to a target site in a patient and adjusting the tension in the implant 42, the suture 46 will be pulled tighter as the tension in the implant increases.

When the tension in the suture 46 reaches a predetermined level, the suture 46 will break or damage the capsule 40, thereby releasing its contents. The contents of the capsule 40 may be a colored liquid, for example, that is detectable when it is released from the capsule so that the surgeon will know that a desired tension level has been achieved. Alternatively, the fluid may be detectable in a manner other than a visual manner. The fluid contained in the capsule may be saline, for example, or any other fluid that will not adversely affect the patient. The outer covering of capsule 40 can be made of a bioabsorbable material so that it can remain in the patient after it has been broken, or it can instead be removed from the patient after it breaks. The suture 46 that was wrapped around the capsule can optionally be left in place within the patient, where it can provide additional reinforcement or support for the implant until in-growth has occurred.

Figure 5:
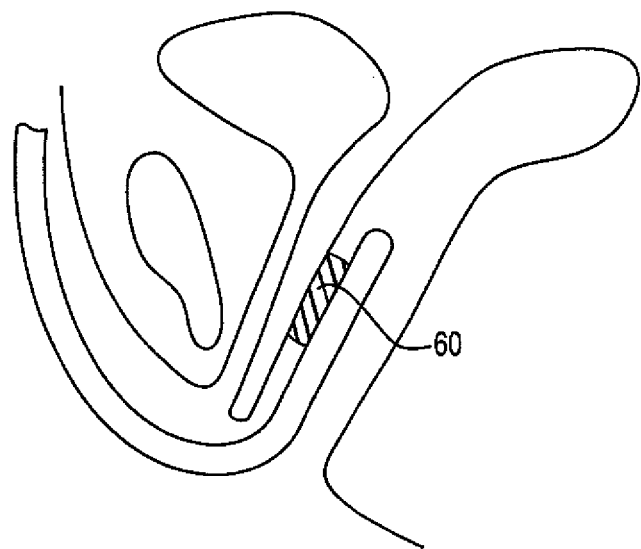
FIG. 5 is a schematic side view of a pressure sensitive device of the invention as it can be positioned within a patient.

FIG. 5 illustrates an exemplary embodiment of an instrumental pessary or other small medical device 60 that can be inserted into a patient (e.g., in the vagina or rectum) and that can be held in place by the muscles of the pelvic floor. The pessary 60 can include a pressure sensitive pad that records when a patient is continent before an implant procedure. A similar pressure device can then be used in the operating room to obtain the same pressure. In this way, the device can be customized to a particular patient in order to give the proper support and to increase confidence. In an alternate exemplary procedure, the pessary is implanted in a temporary manner and a separate measuring device is positioned in the urethra to measure the pressure. The same device can be used in the operating room, which can be integrated with or can replace a catheter.

Figure 6A:
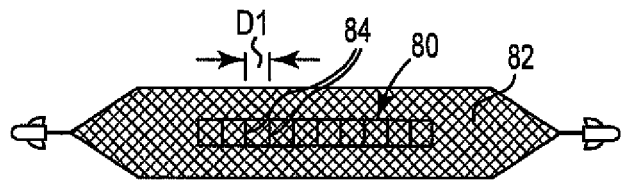
FIGS. 6A and 6B are top views of an exemplary embodiment of a tension indicator of the invention positioned relative to an implant.
Figure 6B:
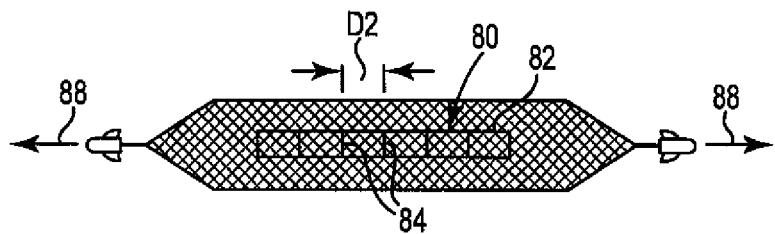
Figure 6C:
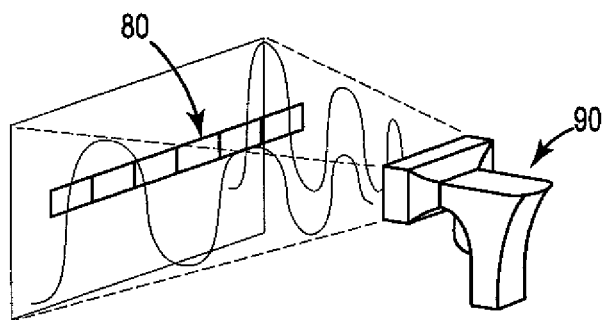
FIG. 6C is a perspective view of the tension indicator of FIGS. 6A and 6B as it can be read by a scanning device.

FIGS. 6A-6C illustrate another exemplary embodiment of a device or feature for measuring tension of an implant. In this embodiment, an indexing strip 80 is positioned along a surface of an implant 82, which may be a mesh implant or sling. The indexing strip 80 can either be integrated into the material of the implant itself or can be a separate structure that is attached to one or both of its surfaces. The indexing strip 80 may also be referred to as a "distance index" or a "bar code", and may include multiple indicators or indicia 84 along its length. These indicators 84 are spaced from each other by predetermined distances, wherein these distances can be the same or different from each other along the length of the indexing strip 80.

FIG. 6A shows the configuration in which the implant 82 is in a relaxed or semi-relaxed condition, with the indexing strip 80 in a first configuration. In this configuration, two adjacent indicators 84 are spaced at a distance D1 from each other. When tension is placed on the implant 82, as is illustrated by the force arrows 88 facing in opposite directions in FIG. 6B, the indexing strip 80 will stretch or expand so that the distance between the same two adjacent indicators 84 will be a distance D2, which is larger than the distance D1 of FIG. 6A. That is, the distance between individual indicators 84 will be larger when the implant is under tension, wherein a particular increase in distance corresponds with a particular amount of tension. A bar code scanner or other device 90 can be used to read the indexing strip 80, as is illustrated schematically in FIG. 6C. The device that reads the indexing strip can then convert this data into information that translates to a corresponding change in the length of the implant due to the tension to which it is subjected. Specific information that relates an amount of stretch or a change in the spacing of the indicators can be predetermined as a function of the amount of tension put on the implant.

Figure 7:
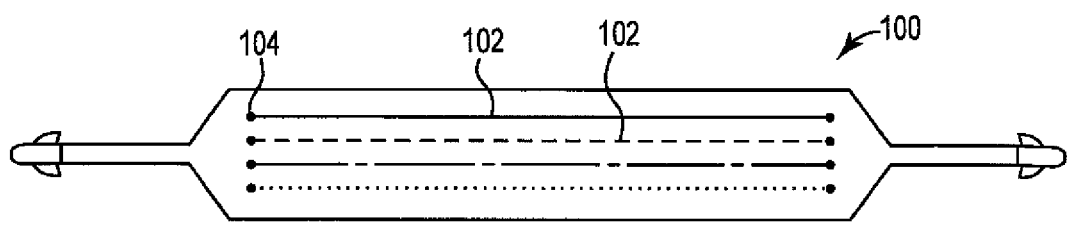
FIG. 7 is a top view of an exemplary embodiment of tension indicators of the invention positioned relative to an implant.

FIG. 7 illustrates an exemplary embodiment of an implant 100 (e.g., a urethral sling or other form of implant), which includes one or more breakable filaments 102, each of which is embedded in/or along a portion of the length of the implant 100. In one embodiment, the implant 100 is a mesh tape that includes multiple filaments 102 embedded within the material of the mesh tape. Alternatively, the one or more filaments can be attached to the surface of the implant 100, such as can be accomplished with adhesives or other securing methods. In any case, the filaments 102 are designed or selected to be breakable at a known tension, where the tension can correspond with a desired tension level in the implant itself. In certain embodiments, the filaments 102 are secured at one or more attachment locations 104, which are spaced at a certain distance from each other when the implant 100 is in a relaxed state.

When multiple filaments 102 are used, they can each have the same or different strengths such that they break when subjected to the same or different amounts of tension. In cases where the filaments are designed to break at different tensions, the various filaments 102 can be monitored while tension is being applied such that one or more of the filaments will break at a relatively low tension, while others will not break until a greater amount of tension is applied. In this way, the user can monitor the amount of tension that is being applied and can thereby customize the amount of tension needed for each individual implantation. If such a multiple-filament system is used, the fact that the load will be redistributed to a smaller number of filaments after each filament breaks should be considered when choosing the various filaments to be included in the filament group.

It is further contemplated that if multiple filaments are used, in accordance with this aspect of the invention, that these filaments 102 can also optionally be color-coded so that a surgeon can monitor the amount of tension being applied. That is, color-coding the filaments 102 so that a first filament having a first color breaks when a first tension is applied and so that a second filament having a second color breaks when a second tension is applied, etc., can provide the user with a particular type of visual feedback that can assist in applying a certain amount of tension on the implant 100.

Figure 8:
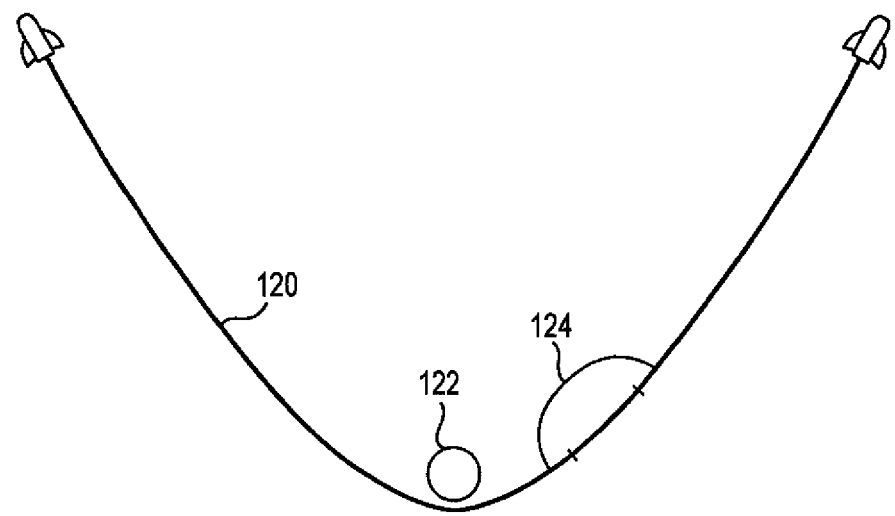
FIG. 8 is a front schematic view of a tension indicator of the invention located relative to an anatomical location of a patient.

FIG. 8 illustrates another exemplary embodiment of an implant 120 in which tension can be measured and/or monitored, as such an implant 120 can be positioned relative to an organ 122 to be supported, such as a urethra, for example. In this case, a device 124 is provided along the length of the implant that is designed to break off at one or more breakaway points with the application of particular amounts of tension. After the device 124 has broken away, tension can remain in the sling.

Figure 9:
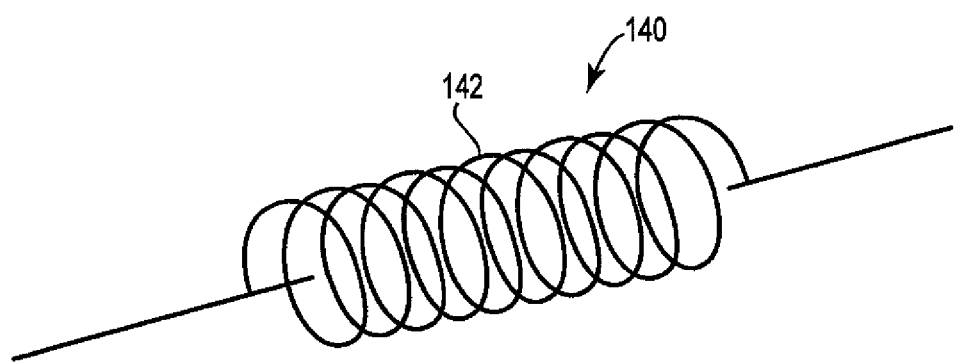
FIG. 9 is an exemplary embodiment of a tension indicator of the invention.

FIG. 9 illustrates an exemplary embodiment of a tension measurement device 140, which comprises at least one winding 142 of material, such as wire, that can be attached to or otherwise associated with a portion of the length of an implant. With this embodiment, an electrical circuit can be checked and removed after the implant is in its desired location. A change of resistance (e.g., higher or lower) will have a corresponding tension correlation that can be read by a surgeon to determine whether a desired level of tension in the implant has been achieved.

Another alternative manner of determining tension in an implant includes exciting a sling and/or suture that is attached or otherwise in functional association with an implant in manner that is similar to processes that are used to excite a musical instrument, such as a guitar string. In operation, the sling and/or suture are excited to cause certain pitches or frequencies to be reached. The amount of tension can be determined by comparing a pitch or frequency of the sling and/or suture to a desired tension level.

Yet another alternative method of determining the amount of load or tension on an implant includes optically characterizing a mesh weave of an implant by first scanning the mesh to determine the shapes and/or sizes of the cells of that mesh. This measurement can be calibrated relative to cell shape and/or size changes that are known to occur as the material is loaded. The cell data can then be compared to the changes in cell shape that actually occur when an implant with those cells is placed under tension in order to determine the amount of tension in the implant.

Figure 10:
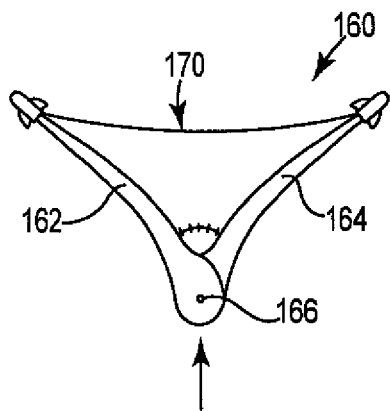
FIG. 10 is a front view of a tension indicator of the invention positioned relative to an implant.

Another tension indicator system 160 is illustrated in FIG. 10, which generally includes first and second arm components 162, 164 that are pivotally attached to each other at their proximal ends at a pivot point 166 in a "wishbone" type of configuration. An implant (e.g. a mesh implant) 170 is illustrated as extending between the distal ends of the first and second arm components 162, 164. The distal ends of the arms 162, 164 are thereby spaced from each other by a specific amount and are attached to the implant 170 at spaced-apart locations. The arm components 162, 164 can pivot relative to each other about the pivot point 166 as the anchors of the implant 170 are pushed into the desired implant areas of the patient. As force or tension is applied to the implant 170, the distal ends of the arms 162, 164 will be forced apart by a corresponding distance. This distance will be correlated to a change in strain implant.

Figure 11:
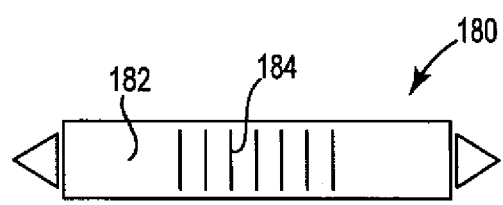
FIG. 11 is a top view of an exemplary embodiment of a tension indicator of the invention positioned relative to an implant.
Figure 12:
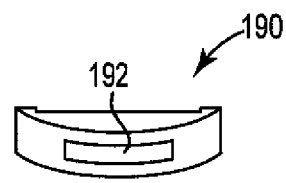
FIG. 12 is a perspective view of a measuring device that can be used with the tension indicator of FIG. 11.

FIGS. 11 and 12 illustrate components of another embodiment of an implant system 180 that generally includes an elongated implant 182 from which anchors extend at opposite ends. The implant 182 includes multiple filaments 184 (e.g., metallic filaments) that extend across its width and that are spaced from each other along its length. These filaments 184 can be embedded into the material of the implant, or can be attached to the surface of the implant, such as by adhesives or other securing material(s). The filaments 184 may extend in a generally perpendicular direction to the longitudinal edges of the implant, or may instead be arranged at an angle relative to the longitudinal edges. Each of the filaments 184 may be spaced at the same or different distance from each adjacent filament 184 along at least a portion of the length of the implant 182.

The implant system 180 further includes a "snap-on" meter 190 or other measuring device that can detect and measure the number of filaments 184 that pass its optical sensor 192, which can be correlated to a particular tension or change in tension in the implant 182, for example. In another embodiment, the meter 190 can instead measure and record the difference in length between filaments 184 as tension is placed on the implant 182, which can then be correlated to a particular tension in the implant 182. The meter 190 can then be removed from the area of the implant 182 after the desired tension in the implant is achieved.

FIGS. 13A-13C illustrate another exemplary embodiment of an implant 200 that generally includes an elongated member having at least one section that has tension-relieving or measurement features. In particular, implant 200 includes an elongated member 204 and areas 206, 208 at its proximal and distal ends, respectively, that are stretchable or expandable in response to a predetermined amount of tension being placed on the implant 200. These stretchable areas include sinusoidal or differently shaped channels 202 that are in a first configuration along their lengths (e.g., see FIGS. 13A and 13B) when the implant is in a relatively relaxed condition. The end areas 206, 208 may be constructed in a number of ways, such as by cutting the channels 202 with a laser or other device, and/or by molding the end portions, either integrally with the central portion or as separate components, that are later attached to the central implant portion.

The implant 200 can then be subjected to a predefined tension that will cause the channels 202 to expand or straighten to be a different shape than when the implant is in its relaxed state (e.g., see FIG. 13C). That is, when the implant stretches or extends in length, as can occur when it is placed under tension, the operator or surgeon can correlate a certain deformation or straightening of the channels 202 with a predefined tension in the implant. Such features can help to prevent or minimize over-tensioning of the implant. Although this embodiment includes two areas where this stretching or deformation of channels can occur, it is understood that a particular implant can include more or less than two of such areas, and that these areas are not necessarily located at opposite ends of the implant, but can instead be spaced inwardly from the ends of the implant.

FIGS. 14A-14C illustrate another embodiment of an implant 220 that operates similarly to the embodiment of FIGS. 13A-13C. Implant 220 generally includes an elongated member having at least one section that has tension-relieving or measurement features. In particular, implant 220 includes an elongated member 224 and areas 226, 228 at its proximal and distal ends, respectively, which include coiled members 222 that can be uncoiled or stretched in response to a predetermined amount of tension being placed on the implant 220. These areas 226, 228 are illustrated with their respective coiled members 222 in a first or relatively compressed condition in FIG. 14A, which occurs prior to any tension being placed on the implant 220. The implant 220 can then be subjected to a predefined tension that will cause the coiled members 222 to be at least partially straightened or uncoiled/deformed, as is illustrated in FIG. 14C, for example. In this way, the implant 220 can be stretched while avoiding over-tensioning, but without yielding. The end areas 226, 228 can be separate components that are integrated with a central mesh area, if desired. Although this embodiment includes two areas where stretching or deformation of coiled members can occur, it is understood that a particular implant can include more or less than two of such areas, and that these areas are not necessarily located at opposite ends of the implant, but can instead be spaced inwardly from the ends of the implant.

Another implant tensioning device is illustrated in FIGS. 15A-15E. In particular, FIGS. 15A-15C illustrate a side view, top view, and front view of a tensioning device 240, respectively, and FIGS. 15D and 15E illustrate a sling or other implant positioned relative to the tensioning device 240. The tensioning device 240 generally includes a base member 242 from which a central support member 244 extends. The central support member 244 is illustrated as having a generally elliptical cross-section, although it can instead have a different shape. In any case, it may be advantageous in some applications for the central support member 244 to have at least one curved surface against which a sling or implant will slide in order for the device to operate more smoothly. Tensioning device 240 also can include two spring members 246 extending from the base member 242 on opposite sides of the central support member 244 and spaced from the central support member 244. Each of the spring members 246 includes a spring or coil extending from the base 242, along with members that extend from the spring or coil that provide for engagement with a surface of an implant. With this embodiment, a sling or other implant 250 can be looped over a top surface of one spring member 246, around a bottom surface of the central support member 244, and over a top surface of the other spring member 246, as is shown schematically in FIG. 15D, for example. The tension on the implant can be increased on one or both of its ends by increasing the opposing forces until the spring members 246 are displaced a certain amount, such as to cause appropriate marks on the implant to be aligned with each other, as is illustrated in FIG. 15E. The tensioning device is preferably removed after the implantation and tensioning processes are complete, although it is possible that the tensioning device can be configured such that it is a permanent component of a tensioning system for a particular implant.

Figure 16A:
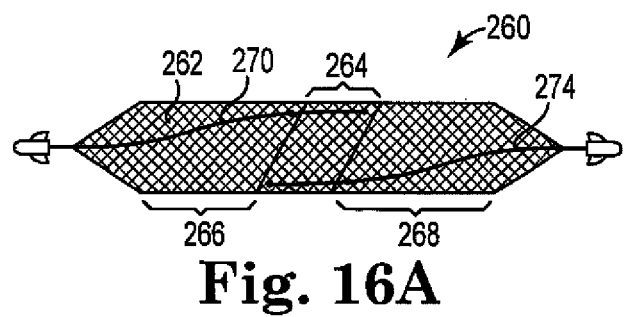
FIGS. 16A and 16B are top views of an exemplary embodiment of a tension indicator of the invention positioned relative to an implant.
Figure 16B:
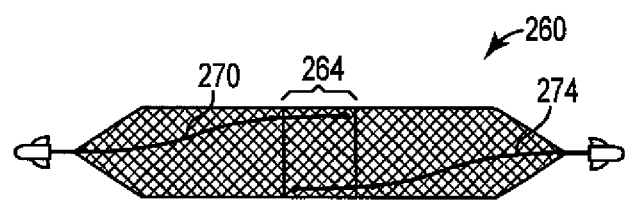

FIGS. 16A and 16B illustrate another embodiment of a tensioning indicator system 260 of the invention. In particular, FIG. 16A illustrates an elongated implant member 262, which may be a mesh material, for example. Member 262 includes a center section 264 and first and second opposite end portions 266, 268 that extend from the center section 264. The center section 264 is configured so that when in the implant 262 is in its relatively relaxed condition, the edges of center section 264 that extend across the width of the implant member 262 are angled (i.e., at an angle other than 90 degrees) relative to the edges of the implant member 262. The implant member 262 further includes an upper suture or chord 270 that extends from its first end, which is attached at a top area of the center section 264, to a second end, which is located generally at a center area of one of the ends (e.g., at the left end of the implant illustrated in FIG. 16A). Similarly, implant member 262 also includes a lower suture or chord 274 that extends from its first end, which is attached at the bottom area of the center section 264, to a second end, which is located generally at a center area of the other of the end of the implant (e.g., at the right end of the implant illustrated in FIG. 16A). With this configuration, the second ends of the upper and lower sutures or chords 270, 274 are pulled in opposite directions relative to the length of the implant to thereby "straighten" the center section 264 relative to the opposite end portions, as is illustrated in FIG. 16B, for example. In one embodiment, the desired or target amount of tension in the implant can correspond to an implant configuration in which the center section 264 has ends that are generally perpendicular to the longitudinal edges of the implant. In other words, the preferred "final" configuration for the implant may include a center section that is square or rectangular in shape.

Figure 17A:
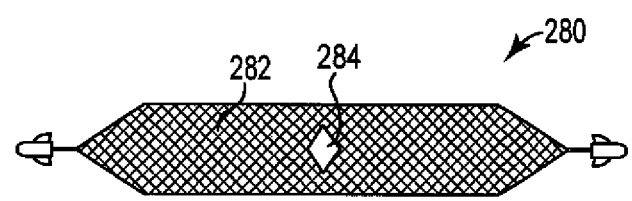
FIGS. 17A and 17B are top views of an exemplary embodiment of a tension indicator of the invention positioned relative to an implant.
Figure 17B:
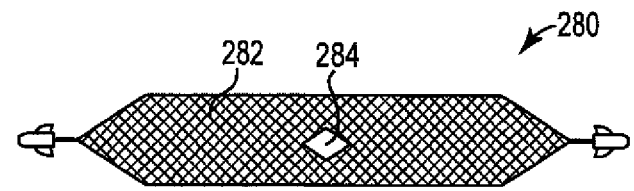

FIGS. 17A and 17B illustrate another exemplary embodiment of a tension indicator system 280, which includes a mesh implant 282 and one or more apertures or markings 284 located at one or more locations along the length of implant 282. Each aperture or marking 284 can have a first shape that corresponds to a first condition of the implant 282 (e.g., an unstressed condition, as is illustrated in FIG. 17A) and a second shape that corresponds to a second condition of the implant 282 (e.g., when the implant is under tension, as is illustrated in FIG. 17B). In order to modify the apertures or markings 284 in such a way, opposite ends of the implant can be pulled in opposite directions until a desired amount of deformation of the markings or apertures 284 is achieved. It is contemplated that the implant 282 can include more than one of these apertures or markings along its length, wherein a device with multiple apertures can include apertures that are configured so that differing amounts of tension on the implant will provide for a corresponding different amount of deformation of these apertures or markings.

Figure 18:
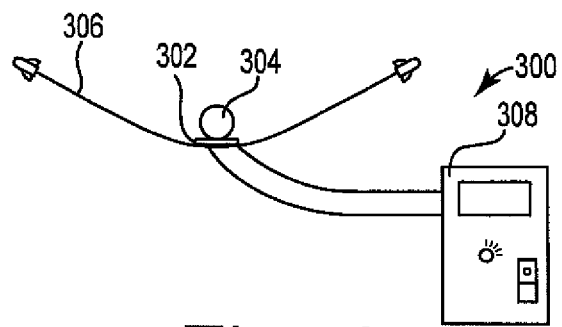
FIG. 18 is a front schematic view of a tension indicator of the invention located relative to an anatomical location of a patient and operatively connected to a monitor.

Another exemplary embodiment of a tension/force/pressure device 300 of the invention is illustrated in FIG. 18, which provides for a force/pressure flex circuit 302 positioned between an implant (e.g., a sling 306) and an anatomical structure (e.g., a urethra 304). The force/pressure flex circuit 302 can be operatively connected (e.g., with wires or wirelessly) to a monitor 308 so that when tension on the implant 306 is increased or tightened, the monitor 308 can record and display the increase in tension. The tension can continue to be increased until the monitor 308 indicates that a desired level of tension has been achieved.

Figure 19A:
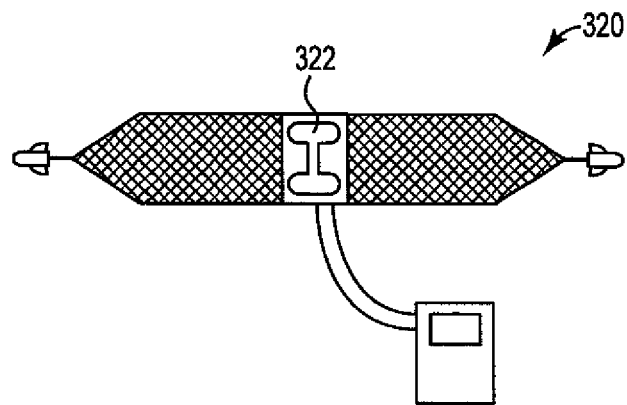
FIGS. 19A and 19B are top views of an exemplary embodiment of a tension indicator of the invention positioned relative to an implant and operatively connected to a monitor.
Figure 19B:
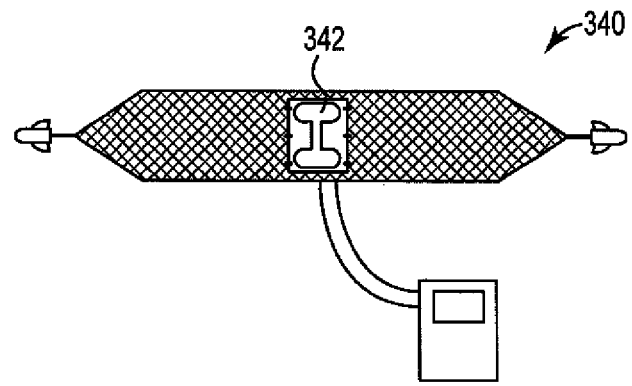

FIGS. 19A and 19B illustrate additional exemplary embodiments of implants 320, 340 that are somewhat similar to that of FIG. 18, except that the implants 320, 340 each include a strain gauge 322, 342, respectively, instead of a flex circuit. Strain gauge 322 can be integrated into the mesh structure of its implant 320, as is illustrated in FIG. 19A. Alternatively, strain gauge 342 can be removably attached (e.g., via clips, sutures, or the like) to implant 340, as is illustrated in FIG. 19B. Tension can be placed on the implants 320, 340 and adjusted until a desired tension level is achieved and/or recorded on their associated monitors. It is noted that when a strain gauge is removably attached to an implant, the strain gauge can be removed when a desired tension level is achieved.

Figure 20A:
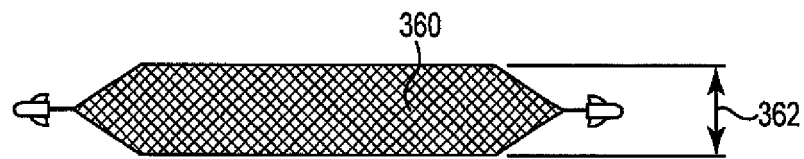
FIGS. 20A and 20B are top views of an implant of the invention in a relaxed state and under tension, respectively.
Figure 20B:
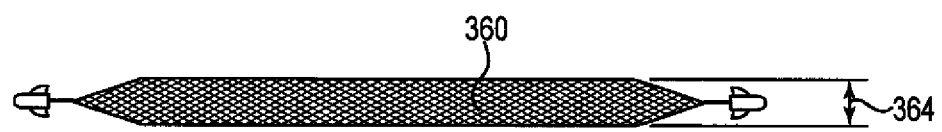
Figure 20C:
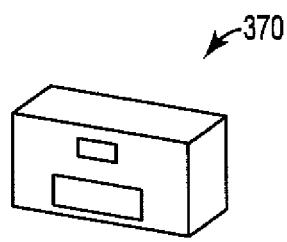
FIG. 20C is a schematic perspective view of an optical tool that can be used with the implants of FIGS. 20A and 20B.
Figure 20D:
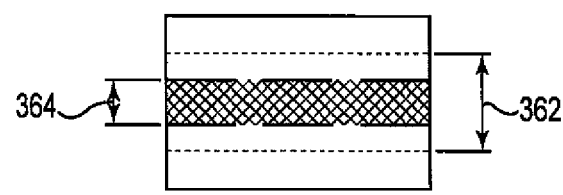
FIG. 20D is a top view of an exemplary recordation of information read by an optical tool of the type illustrated in FIG. 20C.

FIGS. 20A-20D illustrate a system for controlling the tension in an elongated implant 360 by measuring and monitoring its width as tension is being applied. In particular, when the tension placed on an implant of this embodiment is increased, it will become elongated in a longitudinal direction, which thereby will cause a corresponding decrease in the width of the implant. That is, implant 360 will have a first width 362 when it is not under tension (see FIG. 20A, for example) that will be at least slightly larger than a second width 364 of the implant when tension has been applied (see FIG. 20B, for example). This change in the width of the implant can be optically measured and monitored, such as with an optical tool 370 that is schematically illustrated in FIG. 20C, until a desired width of the implant 360 has been achieved. FIG. 20D shows an exemplary visual result that can be recorded by an optical tool, in which the relaxed condition of an implant having a width 362 is represented by the outer dashed lines, and in which the stressed or tensioned condition of that same implant having a width 364 is represented by the inner dashed lines.

With any of the embodiments of implants or implant systems described herein, it is understood that the implant may include an implant member having two ends, each of which includes an anchor, such as a self-fixating tip or tissue anchor. However, other types of implants are also contemplated, such as an elongated mesh extension portion that is a component of a larger implant system or component. The anchors at the ends of the implants may be designed to engage with a distal end of an insertion tool that can push the anchor into its desired position within a patient, such as at the soft tissue of an obturator foramen. In addition, the tensioning devices described herein can be constructed of various biocompatible materials, and/or at least some of the components of the tensioning devices or systems can be bioabsorbable and/or biodegradable after a predetermined period of time, such as can be accomplished with components made of absorbable polymers.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the references incorporated herein are envisioned for use with the present invention as well. All patents, patent applications, and publications cited herein are hereby incorporated by reference in their entirety as if individually incorporated, and include those references incorporated within the identified patents, patent applications and publications.

The invention claimed is:

1. An implant system for treating a pelvic condition, the implant system comprising:
   an implant member defining a longitudinal axis along a length of the implant member; and
   at least one tension indicator operatively coupled to the implant member, the at least one tension indicator having a first end portion and a second end portion, a distance between the first end portion and the second end portion defining a longitudinal axis, the at least one tension indicator configured to provide an indication of tension to a user during a process of implanting the implant member in response to a force applied to the at least one tension indicator exceeding a threshold level, the at least one tension indicator being configured to bend such that the first end portion and the second end portion move toward each other,
   wherein the longitudinal axis of the implant member being disposed at a non-zero angle with respect to the longitudinal axis of the at least one tension indicator.

2. The implant system of claim 1, wherein the at least one tension indicator has a substantially planar configuration and a curved configuration, wherein the at least one tension indicator moves from the substantially planar configuration to the curved configuration in response to the force exceeding the threshold level.

3. The implant system of claim 1, wherein the implant member includes a mesh implant.

4. The implant system of claim 1, wherein the implant member includes a first end portion and a second end portion, the implant member including a first anchor coupled to the first end portion, the implant member including a second anchor coupled to the second end portion.

5. The implant system of claim 1, wherein the at least one tension indicator includes a metal frame covered by a flexible covering material.

6. The implant system of claim 1, wherein the at least one tension indicator has a rectangular shape.

7. The implant system of claim 1, wherein the at least one tension indicator is configured to be positioned between the implant member and a urethra of a patient.

8. The implant system of claim 1, wherein the at least one tension indicator is formed of a metal material.

9. The implant system of claim 1, wherein the at least one tension indicator is a shape-changing tension indicator.

10. An implant system for treating a pelvic condition, the implant system comprising:
    an implant member defining a longitudinal axis along a length of the implant member; and
    at least one tension indicator operatively coupled to the implant member, the at least one tension indicator having a substantially planar configuration and a curved configuration, the at least one tension indicator configured to move from the substantially planar configuration to the curved configuration in response to a force applied on the at least one tension indicator exceeding a threshold level,
    wherein the at least one tension indicator having a longitudinal axis, the longitudinal axis of the implant member being disposed at a non-zero angle with respect to the longitudinal axis of the at least one tension indicator,
    the at least one tension indicator having a length greater than a width of the implant member.

11. The implant system of claim 10, wherein the at least one tension indicator is formed of a metal material.

12. The implant system of claim 10, wherein the at least one tension indicator is a shape-changing tension indicator.

13. An implant system for treating a pelvic condition, the implant system comprising:
    an implant member having a first end and a second end, a distance between the first end and the second end defining a longitudinal axis; and
    at least one tension indicator operatively coupled to the implant member, the at least one tension indicator having a first end portion and a second end portion, a distance between the first end portion and the second end portion defining a longitudinal axis, the at least one tension indicator configured to provide an indication of tension to a user during a process of implanting the implant member in response to a force applied to the at least one tension indicator exceeding a threshold level, the at least one tension indicator configured to move such that the first end portion moves towards the second end portion of the at least one tension indicator, the at least one tension indicator being formed of a metal material,
    wherein the longitudinal axis of the implant member being disposed at a non-zero angle with respect to the longitudinal axis of the at least one tension indicator.

14. The implant system of claim 13, wherein the tension indicator is a shape-changing tension indicator.

* * * * *